(12) United States Patent
Kadiyala et al.

(10) Patent No.: US 6,174,333 B1
(45) Date of Patent: *Jan. 16, 2001

(54) BIOMATRIX FOR SOFT TISSUE REGENERATION USING MESENCHYMAL STEM CELLS

(75) Inventors: Sudhakar Kadiyala, Baltimore, MD (US); Arnold I. Caplan, Cleveland Heights; David J. Fink, Shaker Heights, both of OH (US); Randall G. Young, Ellicott City, MD (US)

(73) Assignees: Osiris Therapeutics, Inc., Baltimore, MD (US); Case Western Reserve University, Cleveland, OH (US)

( * ) Notice: Under 35 U.S.C. 154(b), the term of this patent shall be extended for 0 days.

This patent is subject to a terminal disclaimer.

(21) Appl. No.: 09/222,688

(22) Filed: Dec. 29, 1998

Related U.S. Application Data

(63) Continuation-in-part of application No. 08/723,260, filed on Sep. 30, 1996, now Pat. No. 5,855,619, which is a continuation-in-part of application No. 08/254,125, filed on Jun. 6, 1994, now abandoned.

(51) Int. Cl.[7] ........................................................ A61F 2/02
(52) U.S. Cl. ............................................................ 623/11.11
(58) Field of Search ................................... 673/11, 12, 13, 673/14

(56) References Cited

U.S. PATENT DOCUMENTS 5,855,619 * 1/1999 Caplan et al. .

* cited by examiner

*Primary Examiner*—David J. Isabella
(74) *Attorney, Agent, or Firm*—Carella, Byrne, et al.; Elliot M. Olstein; William Squire

(57) ABSTRACT

An implant for repair of a tissue defect comprises a plurality of physiologically compatible load-bearing sutures for securing under tension tissue adjacent to the defect to be repaired, the sutures for supporting a tissue reparative cell mass in the defect and a tissue reparative cell mass supported thereby. The sutures have a central portion encapsulated in a cell containing matrix which is contracted under a tensile load by the cells thereof and formed into a mat sheet during the contraction. Spring metal wires hold the sutures in tension during the contraction. The matrix is a collagen gel or other material which the cells contract, the cells comprising human mesenchymal stem cells. The mat sheet is then rolled into a spiral roll with the sutures extending from opposite roll ends to form the desired implant. Different embodiments are disclosed.

21 Claims, 3 Drawing Sheets

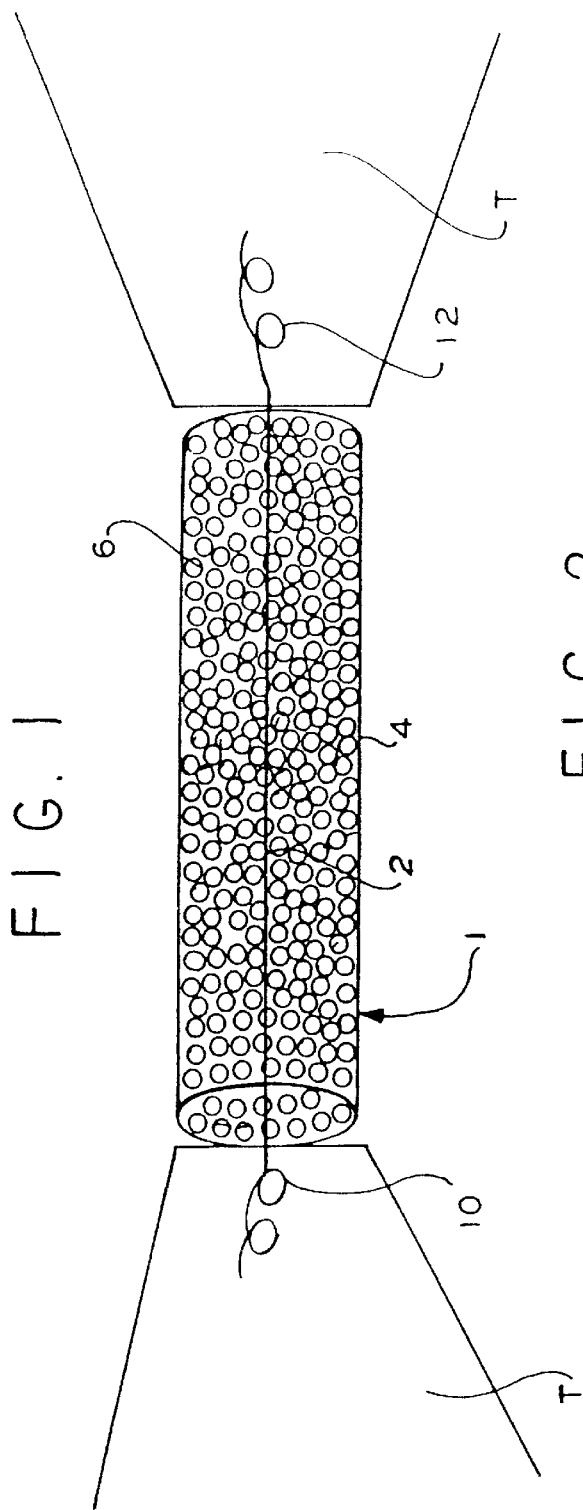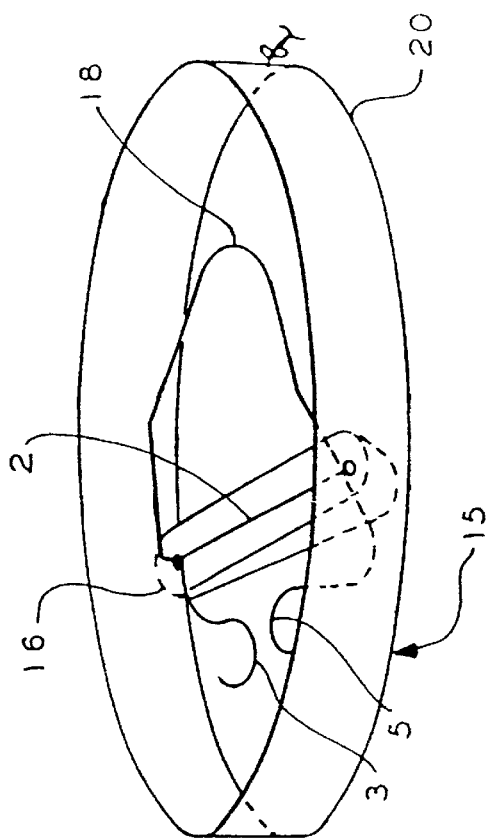

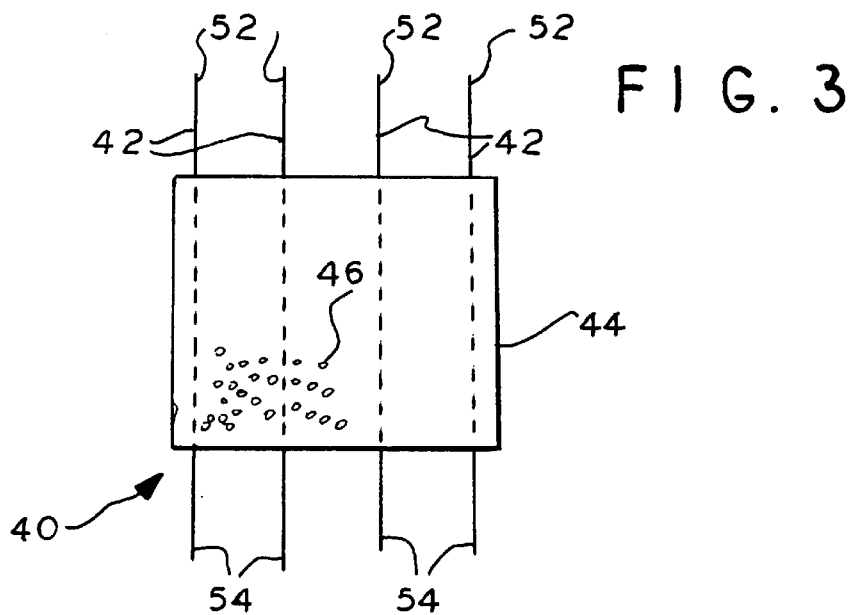
FIG. 3
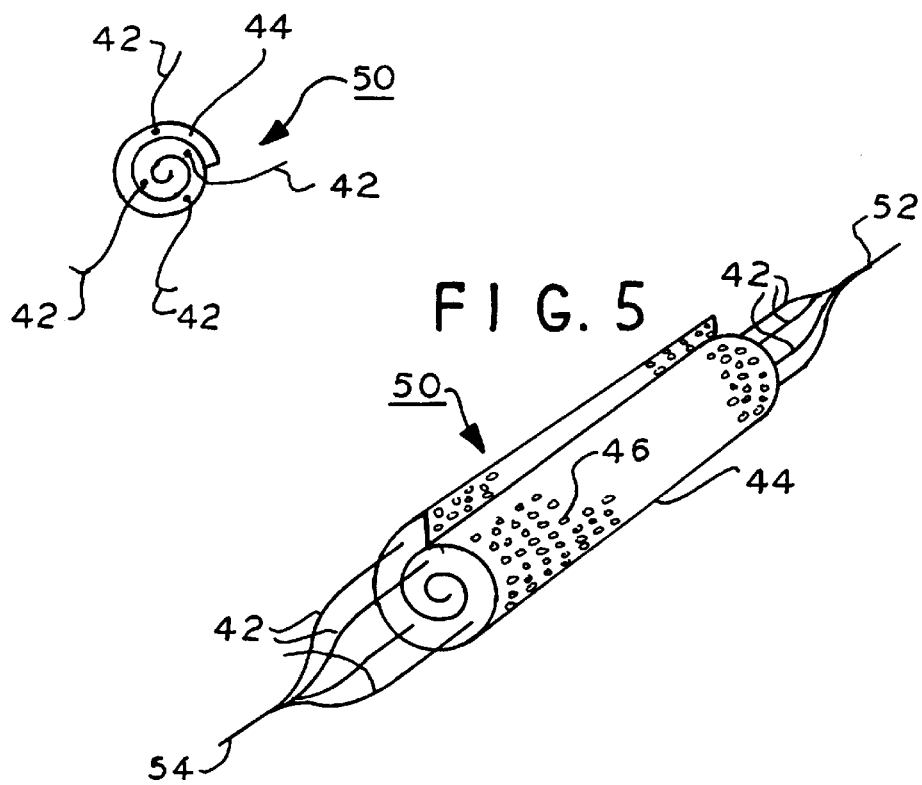
FIG. 4
FIG. 5

BIOMATRIX FOR SOFT TISSUE REGENERATION USING MESENCHYMAL STEM CELLS

This application is a continuation-in-part application of U.S. Ser. No. 08/723,260 filed Sep. 30, 1996, U.S. Pat. No. 5,855,619, which is a continuation-in-part application of U.S. Ser. No. 08/254,125, filed Jun. 6, 1994, abandoned.

CROSS REFERENCE TO RELATED APPLICATIONS

Of interest is commonly owned copending application U.S. Ser. No. 09/039,127 entitled "Uses for Human Mesenchymal Stem Cells" filed Mar. 13, 1998 in the name of Bruder et al. and incorporated by reference in its entirety herein.

BACKGROUND OF THE INVENTION

In the context of skeletal tissue repair, tissue regeneration therapy is the local application of autologous (host-derived) and allogeneic (non-host derived) cells to promote reconstruction of tissue defects caused by trauma, disease or surgical procedures. The objective of the tissue regeneration therapy approach is to deliver high densities of repair-competent cells (or cells that can become competent when influenced by the local environment) to the defect site in a format that optimizes both initial wound mechanics and eventual neotissue production. For soft tissue repair, it is likely that an implant vehicle(s), will be required to 1) transport and constrain the autologous cells in the defect site and 2) provide initial mechanical stability to the surgical site. In an optimal system, it is likely that the vehicle will slowly biodegrade at a rate comparable to the production of neotissue and development of strength in the reparative tissue (1).

The tissue regeneration therapy approach contrasts significantly with more passive approaches to wound repair in which no attempt is made to deliver or to recruit reparative cells to the defect site. For example, in the case of anterior cruciate ligament (ACL) repair with synthetic (presumably "inert") polymer grafts, the healing process depends entirely on local cellular responses to initiate and control the incorporation of a permanent implant (2).

Recently, more active devices have been tested using matrix scaffolds designed to deliver and/or to direct cellular processes. These have included, for example, tendon or ACL repair (3–7), meniscus repair (8–11) and articular cartilage repair (12–15). Alternatively, the use of locally delivered peptide factors, intended to stimulate recruitment of reparative cells and their attachment and/or differentiation, have also been investigated (16–19).

In perhaps the best documented tendon repair experiments to date, Silver, Dunn and their colleagues have described extensive investigations of the performance of collagen fiber prostheses for Achilles tendon (3–5) and anterior cruciate ligament (ACL) (6,7) repair in rabbits. They report that at 52 weeks postimplantation in the Achilles tendon defect, the reconstructed tendon (prosthesis+repair tissue) was about 66% as strong as the normal tissue for all implants tested, including an autologous tendon graft and glutaraldehyde— or carbodiimide-crosslinked collagen fiber composites (5). Both the autologous implants and the carbodiimide-crosslinked prostheses were observed to biodegrade rapidly, then regain strength rapidly as new tissue was produced. Glutaraldehyde cross-linked prostheses biodegraded much more slowly in the Achilles tendon model and became surrounded by a thick capsule that eventually stopped the degradation process. While the neotendon developed in these studies was similar to normal, it was not identical. For example, the crimp angle of the neotendon collagen was similar to normal tendon in all implants, but the length of the neotendon crimp was less than about 30% of normal for the collagen prosthetic devices. In addition, the moduli of the neotendons formed from the more rapidly degrading implants (autologous tendon and carbodiimide-crosslinked collagen fibers) were significantly lower than for normal tendon. Finally, the neotendon observed did not assemble with the fascicle microarchitecture of normal tendon. These researchers conclude that the rate of degradation of the prosthesis, and the consequent transfer of load to the new tissue, may be as important as the initial prosthesis tensile strength in determining the ultimate properties of the repair tissue (5). A similar generation of neoligament was observed in the ACL implants after 20 weeks, although the recovery of strength of the tissue may be somewhat slower in the avascular synovial environment (7).

Based on this evidence, it is clear that at least in the healthy animal, repair-competent cells can be recruited from the tissues surrounding defects in tendons and ligaments, and that these cells will initiate the production of neotissue. It remains unclear from these investigations to what extent the recruited cells represented differentiated phenotypes (e.g., tendon fibroblasts), as opposed to undifferentiated pluripotent stem cells, or whether increased numbers of such cells would enhance the rate of synthesis or the microarchitecture and mechanical properties of the neotissue produced.

Many cell-mediated processes related to the production of skeletal tissue depend on the number of cells involved, both in the rate and magnitude of the effect. For example, in the in vitro production of connective tissue, the rate of collagen gel contraction by fibroblasts encapsulated in the gel is dependent on the number of cells present in the culture (20). A similar gel-contracting activity has also been correlated with cell density-dependent secretion of a contraction-promoting factor by endothelial cells (21). In addition, the extent of fibroblast orientation in cultures grown on collagen gels is directly related to the initial cell density (22). This cell orientation effect has been correlated with the observation of "organizing centers" in the culture, the number of which has been suggested to be a direct indicator of morphogenetic capacity at the molecular and cellular levels (23).

Cell density-dependent differentiation was clearly demonstrated in the culture of chick limb bud cells (24). When cultured at very low density ($10^6$ cells/35 mm dish), these cells do not exhibit chondrogenic or osteogenic properties. At "intermediate" cell culture densities ($2\times10^6$ cells/35 mm dish), the cells exhibit the maximum frequency of osteogenesis, while at still higher density ($5\times10^6$ cells) the maximum frequency of chondrocyte phenotypes is observed.

In each instance cited above, the number of cells initially present strongly influences the nature of cell-mediated processes involved in skeletal tissue formation and the rate at which these developmental and physiological processes occur. Therefore, in the reparative processes of skeletal tissues, Caplan and coworkers have hypothesized that some minimum threshold of cell number may be required at the repair site before formation of "normal" neotissue can occur (25). Furthermore, in many cases, this minimum threshold may exceed the number of recruitable reparative cells, including less committed cells that can differentiate to repair competent phenotypes; therefore, the extent to which the reparative process can occur may be limited by this single parameter.

Preliminary investigations of the tissue regeneration therapy approach have recently been conducted in a tendon repair model in the Achilles tendon of the rabbit (25). There were three components to this model: the defect, the cells and the vehicle to deliver the cells to the defect site. The delivery vehicle in this model must restrain the cells at the defect site, stabilize the tissue mechanics, then slowly biodegrade as new tissue is produced.

SUMMARY OF THE INVENTION

The present investigators through the present invention have made it possible to achieve tissue repair of connective tissue defects, such as tendon, ligament, fibrocartilage and articular cartilage, with greatly enhanced, on the order of doubled, biomechanical strength and stiffness of the reparative tissue produced by the aligned and elongated cells in their "biomatrix" implant compared to defects repaired only by constitutive recipient tissue. In addition, the defect site resolves towards complete repair much more rapidly when using the biomatrix device and the "regenerative tissue repair" procedure of the invention.

The present invention relates to a device for implantation of any type of cells that will effect tissue repair. Although the invention is not limited to any particular cell type, a particularly preferred embodiment includes human mesenchymal stem cells (MSCs), or any of their committed or differentiated progeny. Such cells are preferably used in combination with other cells to form constructs in a single implant device. The cells are preferably obtained from the animal for which the implant is intended, and can preferably be culture expanded prior to implant. The animal is preferably a human.

An implant according to the present invention for repair of a tissue defect in an animal in need thereof comprises a contracted gel matrix formed in a planar mat having a length and a width forming a broad surface in a thickness relatively smaller than the width and length and mesenchymal stem cells within the contracted gel matrix, the cells having contracted the gel matrix, the matrix having been contracted in tension in a given direction.

An implant according to a further aspect of the present invention includes at least one elongated support member extending in the given direction through and embedded within the matrix and having free opposing ends extending beyond the contracted matrix.

The cells preferably are human mesenchymal stem cells (MSCs).

In a further aspect, the mat is rolled against itself and formed into a spiral roll configuration.

In a further aspect, a plurality of the at least one elongated support members are in spaced side by side relation in the mat, each member having free opposing ends.

The support members are preferably biodegradable filaments.

BRIEF DESCRIPTION OF THE DRAWING

FIG. 1 is an isometric diagrammatic view of a preferred embodiment of a biomatrix implant according to the present invention;

FIG. 2 is an isometric diagrammatic view of the biomatrix implant of FIG. 1 as it is being prepared under tension in a mold assembly;

FIG. 3 is a plan diagrammatic view of a further embodiment of the present invention in an intermediate stage;

FIG. 4 is an end view of the embodiment of FIG. 3 rolled up to form an implant according to a second embodiment of the present invention;

FIG. 5 is an isometric view of the embodiment of FIG. 4;

DETAILED DESCRIPTION OF PREFERRED EMBODIMENTS

Figure 6:
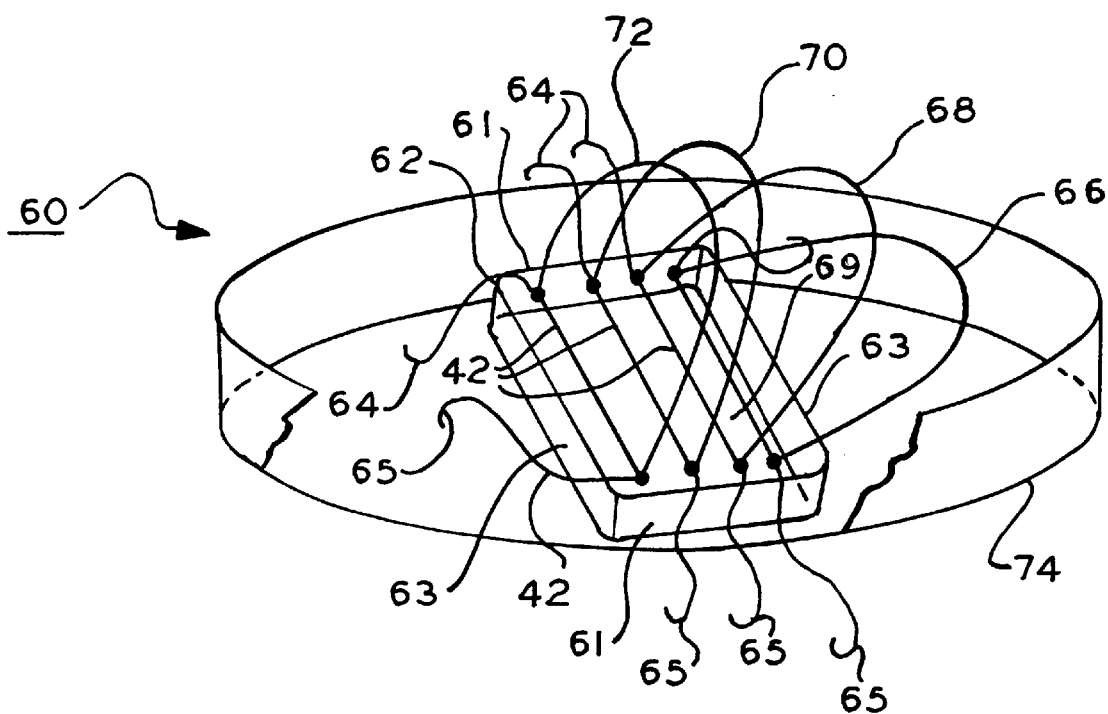
FIG. 6 is an isometric diagrammatic view of the biomatrix implant of FIGS. 4 and 5 as it is being prepared under tension in a mold assembly.

In a specific embodiment of this invention, methods have been and are demonstrated for culturing MSCs or tendon fibroblasts onto double-needle Dexon sutures by causing the cells to contract collagen gels around the central region of the sutures. An autologous or allogeneic cell/collagen gel/suture composite device can be directly implanted between the free ends of full-thickness tendon defects, such as for repair of the human Achilles tendon, ligament such as for repair of the anterior cruciate ligament, or fibrocartilage such as meniscus, or the disc of the temporomandibular joint, or for repair of articular cartilage. With respect to allogeneic cells reference is made to the aforementioned copending application U.S. Ser. No. 09/039,127 incorporated by reference herein. This application discloses that allogeneic MSCs can be used similarly as autologous MSCs and such allogeneic MSCs may be successfully implanted, although autogolous MSCs are preferred.

In the embodiment shown in FIG. 1, implant 1 comprises a strand of suture material 2 and a gel matrix 4 containing reparative cells 6 and which has been contracted around the central portion of suture 2. Suture 2 has free ends 10 and 12 which are used to rejoin the tissue T adjacent the defect. As shown free ends 10 and 12 have been sewn into the body of the tissue thereby not only holding the ends of the tendon in place but also holding gel matrix 4 in position in the defect.

FIG. 2 shows a mold assembly 15 which can be used to form an implant of the invention. Mold assembly 15 includes mold 16 in which the cell-containing gel matrix is formed around suture 2 which is shown here with needles 3 and 5 at the ends thereof. Tension wire 18 which holds suture 2 under tension in mold 16 and incubation dish 20 in which the matrix preparation is incubated to set the gel. The tension applied to the gel matrix while the gel is being contracted (which as shown in FIG. 2 can be applied by tension wire 18) causes the cells within the matrix to align in the direction in which tension is applied to the matrix. As shown in FIG. 2, tension wire 18 causes the gel matrix during contraction to be placed under tension in the axial or longitudinal direction.

While one preferred material for the gel matrix employed is composed of purified Type I collagen fibrils, other materials that can likewise be used include, for example, 1) cell-contracted collagen gels containing other components of the extracellular matrix, such as proteoglycans or glycosaminoglycans, glycoproteins (fibronectin, laminin, and so on), other collagens (e.g., Types II or IV), elastin and/or bioactive peptide growth factors or cytokines; 2) other biopolymers such as fibrin; 3) synthetic biodegradable fibers made from such polymers as polylactic or polyglycolic acids, polycaprolactones, or polyamino acids, or their copolymers, which could be cast or wound into or onto the suture; or 4) composite structures such as collagen/polylactic acid structures.

In addition to simple single-filament sutures, multifilament devices produced by braiding, weaving or knitting biodegradable fibrous materials including sutures or collagen fibers or the like can also be used. Cells could in general be attached to such devices by cell-mediated processes such as contraction of collagen gels, or by non-cell-mediated physical or chemical processes such as gel-casting gelatin, or a winding of cell-containing fibrous or membranous structures around the device. Such implantation devices could have one or more needles attached at each end of the device to facilitate fixation to soft or hard tissues, and could be of a variety of geometries including planar, cylindrical or tubular construction, depending upon the specific tissue to be repaired, the mode of fixation of the implant and/or the method used to attach the cell-containing biomatrix combination to the implantation device.

A specific embodiment of this is described in the example below.

EXAMPLE 1

A mold assembly was used to prepare an implant for repair of a tissue defect in accordance with the invention. Small, glass cylinders, 5 mm×27 mm, which had had their ends fused shut, were cut longitudinally through the center to form glass, canoe-shaped molds. Stiff surgical wires were bent to form small, bow-shaped tension wires with ends shaped to set just 2 mm deep into the glass molds. The glass mold was placed into a 100 mm culture dish with a suture spanning the tension wire situated in the center of the mold in preparation for the gel suspension to be poured.

Autologous mesenchymal stem cells ($4 \times 10^6$ cells) were suspended in 0.5 ml of 2× DMEM-LG and mixed thoroughly to create a single-cell suspension. Then 0.5 ml sterilized type I collagen solution (Pancogene S™), Gattefossé S A, Lyon, France; 3 mg/ml; dialyzed into 0.001M HCl was added to the cell suspension and pipetted up and down to form a homogenous suspension of cells in the gel. This gel suspension was immediately poured into the prepared glass mold in the culture dish. The lid was placed over the dish and it was put into the incubator at 37° C. for 15–20 minutes to set the gel. After gelation was complete, the dish was flooded with medium without serum until the glass mold was covered and put back into the incubator for 4–6 hours. Contraction of the gel by the cells occurred to the extent that the gel was detached from the walls of the mold and decreased in diameter and length by about 10%. If the cells are cultured in this apparatus for approximately 20 hours, the gel contracts to approximately 60% of its original radial dimension. At the 4 hour time point, the gel was firmly attached to the central suture, such that the suture and tension spring could be lifted out of the medium, the tension spring removed, and the gel implanted in the surgical defect as described.

Tissue repair devices prepared by this procedure were implanted in rabbit Achilles tendon defect model either with or without a Vicryl sheath. Histological observations from these implants at 1, 3 and 8 weeks indicate that neotendon tissues are formed as early as 1–3 weeks by this procedure. These early neotendon tissues are morphologically similar to tissues produced from tendon cell or MSC implantation in the Vicryl sheath repair model at later timepoints.

EXAMPLE 2

MSC/Biomatrix Construct

Mesenchymal stem cells (MSCs) cultured to confluency at the end of first passage are suspended in serum-free medium at a concentration of 8 million cells/milliliter. The collagen matrix consists of Type I bovine skin-derived collagen at 3 mg/ml. A 250 μl aliquot of this collagen suspension is combined with autologous MSCs ($8 \times 10^6$ cells/ml) suspended in 250 μl of 2× DMEM-LG and mixed thoroughly to create a single-cell suspension. The MSC concentration then becomes 4 million cells/milliliter. This cell suspension was immediately poured into the system of FIG. 2 composed of a wire spring device holding polyglycolic acid suture (Maxon Davis and Geck, size 4-0) in tension which is set into a glass trough approximately 1 cm in length with a volume of 500 μl.

The lid was placed over the dish and it is put into the incubator at 37° F. for 15–20 minutes to set the gel. After gelation was complete, the dish was flooded with medium without serum until the glass mold was covered and put back into the incubator for 4–6 hours. Contraction of the gel by the cells occurred to the extent that the gel was detached from the walls of the mold and decreased in diameter and length by about 10%. If the cells are cultured in this apparatus for approximately 20 hours, the gel contracts to approximately 60% of its original dimension in the radial direction. At this point, the gel was firmly attached to the central suture, such that the suture and tension spring could be lifted out of the medium and implanted in the surgical defect as described. Specific methodologies of mesenchymal stem cell recovery culture have been described (see Caplan, et al. U.S. Pat. No. 5,486,359 (1996); Caplan, et al. U.S. Pat. No. 5,226,914 (1993); and Caplan, et al. U.S. Pat. No. 5,197,985 (1993)).

Suture Tensioning Device

The tension and reproducibility of the spring device used in the implant construction were tested. Suture pretensioning springs were prepared by bending 0.035" diameter stainless steel K wires (Zimmer, Warsaw, Ind.) around a mandrel. The distance between the ends of the K wire was set at about 7 cm. Each suture was pre-tensioned by compressing the spring so that its ends were 10 mm apart. To determine the reproducibility in tensioning the suture, the variability in the initial shape of the springs and the ability of the compressed spring to provide a uniform restoring force were examined. Seven springs were tested. For the unloaded springs, the initial distance between the ends and the angle formed by the two legs of the spring were then measured. The springs were mounted in grips on an Instron 8501 testing machine and the tips compressed until they were 10 mm apart.

No significant differences were observed among the springs for any of the three parameters measured ($p > 0.05$). The initial distance between the spring ends was 68.7±3.4 mm (mean±one standard deviation) and the initial angle between the legs of the spring was 58.0±3.8 degrees. The mean restoring force produced by the spring when the ends were compressed to 10 mm was 4.9±0.7N. Moreover, the relationship between tip-to-tip displacement and the spring restoring force was almost linear over the entire displacement range. Thus, the K wire provides a simple, sterilizable, and reproducible means for pretensioning the MSC/biomatrix/suture construct used to create the implant devices.

Surgical Model

With a rabbit anesthetized and in lateral recumbency, the lateral aspect of the limb was incised over the Achilles tendon region from the gastrocnemius to the calcaneus. Rabbit Achilles tendon consists of three tendon bundles encased in a common tendon sheath, two of which are fused bundles of the material and medial tendons of the gastrocnemius. The surgical defect was always created in the lateral tendon bundle. After incising through the tendon sheath, the superficial digital flexor was reflected medially to expose the lateral bundle. A gap defect one centimeter in length was created in the lateral bundle, beginning from a point about 8 mm proximal to the calcaneus. Defects received the contracted MSC/biomatrix construct (=treated) sutured across the gap in one limb, or a tension suture alone in the pattern of a modified Kessler (=control) in the contralateral limb. The tendon sheath was then closed along the length of the implant using a simple continuous pattern and the skin was closed with a continuous subcuticular suture.

Biomechanical Testing

After sacrifice, the paired tendons were immediately frozen. On the day of testing, left-right pairs of tissues were removed randomly, thawed and dissected, each one to create a full length tendon with a healing scar, proximal muscle sheath, and distal bone block. The sheath and bone block were used to grip the tendon for axial testing. The full length of each tendon was recorded along with the width and thickness at three locations along the scar (to compute cross-sectional area). Dye lines were placed at the proximal and distal edges of the scar to visualize where failure occurred during testing.

Each specimen was placed in a bath of warm saline (37° C.) mounted on an Instron 8501 testing system. Each tissue was tested to failure at a moderate strain rate (20%/second) while monitoring failure with video camera. In all cases, failure was initiated within the repaired gap region of the test sample. Five structural parameters were computed (stiffness of the tissue in the linear region, the maximum force at failure, the displacement to maximum force, the energy to maximum force, and the energy to failure). Using initial length between the grips and the cross-sectional area, five material parameters were computed (modulus of the tissue in the linear region, the maximum stress, the strain to maximum stress, and the strain energy densities to maximum stress and failure stress).

Thirty-nine paired rabbit Achilles tendon repairs were blindly tested. Thirteen pairs were evaluated at three time points after surgery: 4 weeks, 8 weeks, and 12 weeks. In addition to the 13 pairs for biomechanical testing, three additional pairs of Achilles tendon repairs were submitted for histological testing. Five untreated tendon specimens were also tested to characterize the "normal" tissue properties.

Statistical Analysis

Both paired and unpaired comparisons were performed on the reduced data. Student t tests were conducted to detect within subject differences (paired left right comparisons) and across subject differences (unpaired comparisons between average treated and average control groups). Power analyses were also performed to determine the number of specimens needed to establish 90% confidence in detecting treatment related differences.

Histology

Specimens for histological evaluation were fixed for a minimum of 7 days in formalin before being placed in a VIP 2000 processor for dehydration through alcohol gradients (70%–100%), xylene, and finally to xylene substitute, Clear Rite (Richard-Allan, Kalamazoo, Mich.). At this point they were processed to PMMA embedding as described in the literature (Sterchi, 1995). Blocks were then cut to produce 5μ sections, affixed to glass slides, and stained with Toluidine Blue and Toluidine Blue/Basic Fuchsin (a Hemotoxylin/Eosin-like stain).

Results/Interpretation

Structural Properties: Normal structural and material properties of rabbit Achilles tendons are shown in Tables 1-A and 1-B.

TABLE 1-A

Structural Properties of the Normal Rabbit Achilles Tendon

|  | Stiffness N.mm | $F_{max}$ N | $Energy_{max}$ N.mm | $Energy_{failure}$ N.mm |
|---|---|---|---|---|
| Means | 36.5 | 189.0 | 555.5 | 901.1 |
| Stand. Dev.'s | 10.6 | 26.8 | 178.2 | 317.2 |
| S.E.M. | 4.7 | 12.0 | 79.7 | 141.9 |
| Number of Specimens | 5 | 5 | 5 | 5 |

TABLE 1-B

Material Properties of the Normal Rabbit Achilles Tendon

|  | Modulus MPa | $Stress_{max}$ MPa | $SED_{max}$ N.mm.mm$^{-3}$ | $SED_{failure}$ N.mm.mm$^{-3}$ |
|---|---|---|---|---|
| Means | 337.5 | 41.6 | 3.9 | 6.7 |
| Stand. Dev.'s | 205.8 | 18.9 | 0.9 | 3.6 |
| S.E.M. | 92.1 | 8.4 | 0.4 | 1.6 |
| Number of Specimens | 5 | 5 | 5 | 5 |

The "percent of normals" data (Table 2) show the average structural values of the treated and control variables as percentages of the normal, surgically unaltered, Achilles tendons at 4, 8, and 12 weeks post-implantation. MSC treatment values appear above corresponding control values.

TABLE 2

Time-Related Changes in Structural Properties of Treated versus Sham Control Rabbit Achilles Tendon Repairs*,+

|  |  | Stiffness | $F_{max}$ | $Energy_{max}$ | $Energy_{failure}$ |
|---|---|---|---|---|---|
| 4 Weeks | Treated (MSC Implants) | 54.2% | 65.8% | 94.5% | 78.8% |
|  | Sham Control | 26.5 | 30.7 | 36.0 | 34.6 |
| 8 Weeks | Treated (MSC Implants) | 62.8 | 60.5 | 65.9 | 59.8 |
|  | Sham Control | 31.1 | 31.9 | 35.3 | 39.2 |
| 12 Weeks | Treated (MSC Implants) | 63.1 | 68.9 | 87.4 | 81.8 |
|  | Sham Control | 31.5 | 30.3 | 30.4 | 32.2 |

*All values are expressed as percent of normal rabbit Achilles tendons.
+All treated values significantly greater than paired sham values for all time points, and all response measures ($p < 0.05$, n = 13)

1. Stiffness (i.e., the ability of the tissue to develop an increment of force for a unit amount of displacement or deformation) of the treated tissues was 54.2% of normal after only 4 weeks, significantly greater than the suture control (26.5%) at the same early time point. This indicated that the treated tissues (and possibly the sutures which have not completely degraded) were already half as stiff as normal tissue; whereas the control tissues (also with suture) were only one-quarter as stiff. The average stiffness of the treated tissues increased modestly thereafter, however, achieving values of 62.8% and 63.1% of normal at 8 and 12 weeks, respectively. The stiffness of the suture controls also increased modestly with time, reaching values of about 31% at both time intervals.

2. The strength of the MSC-treated tissues was regained quickly at 4 weeks; treated tendon supported two-thirds (65.8%) of the maximum force (i.e., ultimate strength) of normal tendon, while the controls supported less than one-third (30.7%) at the same time point. This means the treated tissue can tolerate a large sudden increase in force up to two-thirds of its normal strength without failing, but the control cannot. These percentages are independent of time post-surgery. Thus: a) the treated tissues are twice as strong as the controls at all time points examined, and b) the strength of both the treated and control tissues remained about the same between 1 and 3 months after surgery.

3. The energies (areas under the force displacement curve) up to maximum force and complete failure for the treated tissues were nearly equivalent to values for normal tendons (94.5% and 78.8%) 4 weeks after surgery. The treated tissues withstood about twice the energy of the suture controls at all time periods. On average, and over times analyzed, the treated tissues required about 60–80% of the energy required for failure of normal tendon, whereas the controls required only 30–40%.

Table 3 summarizes the average values of the treated and control material parameters as percentages of the normal, surgically unaltered, Achilles tendons at 4, 8, and 12 weeks post-surgery. The material properties are derived from structural properties by normalizing to initial specimen areas and lengths. Since these material properties are independent of tissue size (length and area), they reflect the inherent properties of the regenerated or repair tissue (plus any suture material which may still be transmitting force).

TABLE 3

Time-Related Changes in Material Properties of Treated versus Sham Control Rabbit Achilles Tendon Repairs*,+

| | | Modulus | Stress$_{max}$ | SED$_{max}$ | SED$_{failure}$ |
|---|---|---|---|---|---|
| 4 Weeks | Treated (MSC Implants) | 15.8% | 20.7% | 24.7% | 20.0% |
| | Sham Control | 9.9 | 11.3 | 11.2 | 9.9 |
| 8 Weeks | Treated (MSC Implants) | 26.8 | 25.4 | 20.6 | 18.1 |
| | Sham Control | 18.4 | 17.3 | 13.3 | 13.7 |
| 12 Weeks | Treated (MSC Implants) | 33.9 | 37.3 | 35.5 | 31.1 |
| | Sham Control | 20.1 | 19.2 | 14.4 | 14.3 |

*All values are expressed as percent of normal rabbit Achilles tendons.
+All treated values significantly greater than paired sham values for all time points, and all response measures ($P < 0.05$, n = 13)

The reported material properties were generally lower as percentages of normal than were the structural properties, reflecting the greater difficulty in re-establishing a normal material as seen in all soft tissue repair models. However, these percentages generally increased with time post-surgery, reflecting the gradual decrease in tissue cross-sectional area resulting from progressive tissue remodeling. (Average cross-sectional areas for treated specimens were 15.1 mm$^2$ at 4 weeks, 10.5 mm$^2$ at 8 weeks, and 7.4 mm$^2$ at 12 weeks, compared to 8.4 mm$^2$ at 4 weeks, 6.3 mm$^2$ at 8 weeks, and 5.4 mm$^2$ at 12 weeks for controls.)

The modules (i.e., the ability of the tissue to develop an increment of stress for a unit amount of strain, measured as the slope of the linear part of the stress strain curve) of the treated tissues was 15.8% of normal after only 4 weeks, while the suture control was only 9.9%. The average moduli for the treated and control tissues increased over time, achieving values of one-third (33.9%) and one-fifth (20.1 %) of normal by 12 weeks, respectively. Thus, both the treated and control tissues increased their moduli over time from relatively low values at one month, with the treated tissue exhibiting a 50% greater modulus at 3 months than the suture control (FIG. 2).

Maximum stress also increased over time for both the treated and control tissues, reading values of about one-third (37.3%) and one-fifth (19.2%) of normal, respectively, by 12 weeks. (FIG. 2) Thus, the maximum force per unit area increased with time for both tissue types, the treated achieving twice the maximum stress of the control by 3 months after surgery.

The energy densities (energies per unit volume) of tissue at maximum stress and failure did not change greatly between 4 and 8 weeks, but achieved about one-third (treated) and one-seventh (control) of normal values by 12 weeks. Thus the unit energy (area under the stress-strain curve) transmitted by the treated repair tissue increases between 8 and 12 weeks, reaching values which are twice the energy density of the controls. (FIG. 2)

Statistical Analysis. The treated and control values (structural and material properties) were compared at each time period using both paired differences (i.e., within animals) and unpaired difference testing (i.e., between group means). Using either paired or unpaired analyses, all but two structural and material properties (maximum displacement and maximum strain) were significantly greater for the treated tissues than for the controls at 4, 8, and 12 weeks after surgery ($p<0.05$, n=13 pairs). The fact that displacement to maximum force and strain to maximum stress were not significantly affected by treatment is not surprising, since studies (not reported here) have shown no effect of any treatment on these two parameters.

EXAMPLE 3

In Vitro Characterization of MSCs in Gels

Histology was performed on MSCs in the MSC/biomatrix construct and in micromass cultures (a 300 ($\mu$l) drop on a 35 mm culture dish). After incubation, these cultures were fixed in 10% buffered formalin and processed for paraffin embedded histology.

Cells in the micromass drop arrayed themselves radially in a starburst pattern with elongated morphology in the central zone and more rounded morphology in the peripheral zone of the gel. In 24 hours, these cells contracted the gel to 30–50% of the original drop diameter (from 11.5 mm to 3.5 mm). The gels contracted inwardly overall, but radially outward from the central zone, leaving a hole in the center of the gel.

Cells in the contracted-gel/suture were elongated and oriented in the longitudinal axis of the suture. These cells contracted the gel radially to about 30% of the original diameter (from 6 mm to 1.5 mm) in 24 hours. There is also axial contraction, but to a lesser extent. The cell density in the gel was high, indicating a high cell viability through the gel preparation and contraction process. The predominant fibroblastic cell type is interspersed with rounded cells in small lacunae in the matrix that compose about 20% of the total population.

These in vitro studies demonstrate that the MSC construct retains cell viability, responds to the surrounding matrix, and aligns cells along the axis of applied tensile loading.

Histological Observations of Achilles Tendon Implants

Interpretation of histological results of rabbit Achilles tendon repair samples requires the use of histological sections achieved through the mid-body of the tissue, so that a significant segment of the suture is visible, for identification of repair tissue properties with confidence. In samples evaluated in this study, about 24 of the 40 samples (20 pairs of tendons) were sectioned clearly along the suture axis. Most sections, treated or controls, contained some regions of disorganized and organized tissue.

4 Week Time Group: Controls

Cells in the non-treated controls exhibit a greater density than in normal un-operated tissue. The cell shape ranges from oval to elongated with fibroblastic morphologies. When viewed at lower magnifications (not shown), oriented fibers and cells in the control repair tissue are observed in thin zones, primarily along the suture. The bulk of the tissue in the repair site is a loose, erratically snaking fibrous connective tissue. The groups of fibers are seen to swirl in and out of the plane with little axial orientation. Birefringence of repair tissue in the control samples was very low as compared to normal tendon fibers.

4 Week Time Group: Treated

The amount of matrix in the 4 week treated samples is noticeably greater than in contralateral controls. Cell density is quite high. Generally, when viewed at lower magnifications, cells have a mixture of rounded and elongated morphologies. The matrix fibers are smaller in diameter than those of normal tissue (20%–30%) and much more varied in diameter. Most fibers in the treated samples are well-aligned parallel to the longitudinal axis of the tendon. These longitudinally oriented fibers of the treated samples form wide avenues along both sides of the central suture with little or no loose connective tissue present. There is little crimp in the fibers at this stage of repair, although this characteristic varies in different regions of the tissue. In the treated MSC-implanted repair tissue, certain groups of fibers demonstrate the same level of birefringence, although with shorter crimp period, as that seen in normal tissue.

8 Week Time Group: Controls

Cells in the control tendons range morphologically from densely populated areas of elliptical cells to less frequent thin elongated cells spaced out over the matrix. More rounded cells appear to synthesize collagen with some crimping. Repair tissue in the controls ranges from loose, very crimped strands to more densely packed filaments, but in general demonstrates the disorganized "whorls" and discontinuous bands of connective tissue. None of this tissue is birefringent under polarized light.

8 Week Time Group: Treated

Treated tendons also demonstrate a range of cellular morphologies from denser areas of elliptical cells to less frequent thin elongated cells. The collagen fibers in the treated samples tend to be grouped in dense cords or bundles organized along the long axis of the tendon. Birefringence of the treated samples demonstrates more densely packed fibers, similar to normal tissue, but with much shorter crimp periods.

12 Week Time Group: Controls

Control repair tissues consistently have less quantity of tissue than treated, with more of the repair tissue present being loose, undulating connective tissue and fewer areas of dense, longitudinally oriented fibers.

12 Week Time Group: Treated

The 12 week treated implants are similar to the 8 week samples. Cells are generally thin, elongated fibroblastic in appearance, and are more densely distributed in matrix than as is seen in normal unoperated tendon, especially along the suture and around knots. In zones more peripheral from the future, the cells are still rounded to oval-shaped, with the same dense distribution, Birefringence reveals the fibers to have crimp periods with shorter periodicity than normal tendon.

When constructions as described above are implanted into full-thickness tendon defects, the incidence of adhesion formation may be greatly reduced in comparison to other constructs in which the cells are not allowed to contract the collagen gel prior to implantation. This suggests that the process of cell-initiated contraction of the collagen gel serves both to constrain the implanted cell population within the boundaries of the gel and to prevent cells initially external to the gel (e.g., muscle-, tendon- or paratenon-derived fibroblastic cells) from entering the contracted gel or attaching to it, thereby resulting in a decrease in adhesion formation.

In a second embodiment, FIG. 3, intermediate stage implant mat 40 comprises four, by way of example, spaced biodegradable filament strands of sutures 42 and a contracted gel matrix 44 containing reparative cells 46. Although the spacing of the strands is not critical, one of ordinary skill in this art will know to employ a spacing, which in relation to the thickness of the mat, provides for sufficient physical integrity of the mat for the various embodiments and implementations desired. What is desired is that the spacing of the sutures is such that a substantially uniform stress is present in the implant when attached to tissue. The cells 46 are contracted around the central portion of each of the sutures 42. Sutures 42 each have free ends 52 and 54 which are used to rejoin the tissue (not shown in this figure) adjacent a defect. The contracted gel matrix 44, in this intermediate stage, is a generally flat sheet of contracted material with the sutures 42 lying generally in a plane forming the mat 40.

The intermediate stage implant mat 40 is then rolled over itself into a spiral roll 50, FIGS. 4 and 5. As noted, the physical integrity of the rolled mat is determined by providing a thickness to the mat based on a given implementation. The greater the thickness, the larger the construct for a given cell-gel matrix construct. The sutures 42 free ends 52 and 54 may then be combined into a single suture at each end for final implantation. The roll 50 forms a spiral of the mat 40 with the contracted cells 46 in overlying contiguous relation. While not being limited to a particular theory, it is believed that the gel of the overlying contiguous surfaces of the mat may join to one another to form a single integral body at the interface therebetween.

As shown, the free ends 52 and 54 of the sutures 42 may be combined into a single free end for sewing into the body of the tissue. In the alternative, the free ends may be sewn into the tissue separately as desired according to a given implementation. The so sewn sutures not only hold the ends of the tendon in place but also hold the gel matrix 44 in position in the defect.

To provide the desired substantially uniform stress on the implant after implantation, in the spiraled configuration, the spacing between strands should be such that for each transverse sectional quadrant or other arc segment of the rolled implant about the longitudinal axis, the number of sutures is preferably uniform. Because of the rolled up configuration of the mat, the implant thus forms a number of overlying layers, e.g., FIG. 4. In a larger implant than that shown, the central most layer will have fewer sutures (not shown) and the outermost layer may have the most sutures. However, the spacing of the sutures in a layer (a layer is one that is at an approximate same radial distance from the central axis in a 360° arc) is to assure a uniform number of sutures in a given quadrant although the number of sutures in a given layer in that quadrant may differ from layer to layer. For example, there may be three sutures (not shown) in the outermost layer in a quadrant and one or no sutures in the inner most layer. Radial alignment of the sutures may also enhance uniformity of stress in a given implementation.

FIG. 6 shows a mold assembly 60 which can be used to form the intermediate mat 40 of FIG. 3. Mold assembly 60 includes a glass mold 62 having a cavity formed by side walls 63, end walls 61 and a bottom wall 69 and in which cavity the cell-containing gel matrix is formed around sutures 42. Preferably the mold bottom wall 69 is formed with parallel elongated grooves or channels (not shown). Each channel receives and holds in place a separate suture. The sutures 42 are shown with optional needles 64 and 65 at the opposite respective ends thereof. Tension wires 66, 68, 70 and 72 hold the sutures 42 under tension in mold 62. The matrix preparation is incubated in incubation dish 74 to set the gel. An optional support (not shown) may hold the tension wires 66, 68, 70 and 72 in position, but this is not necessary. The support may be a stand (not shown) with a clamp (not shown) attached thereto, for example. The tension applied to the sutures and thus to the gel matrix via the sutures while the gel is being contracted (which tension, as shown in FIG. 6, is applied by stiff resilient spring steel tension wires 66, 68, 70 and 72). This tension causes the cells within the matrix 44 to align in the direction in which tension is applied to the matrix, i.e., along the length dimension of the sutures.

In FIG. 6, the intermediate stage implant mat 40 sutures 42 are simultaneously placed in substantially identical tension as described above. However, the tension may vary somewhat among the sutures. More or fewer sutures may be employed according to a given implementation.

In the alternative, a top plate (not shown) may also be included overlying the mold bottom wall and may also have grooves according to a given implementation. In a further alternative, in place of grooves in the bottom wall, opposing end walls 61 adjacent to the suture ends may have holes formed therethrough. The free ends of the sutures are then passed through a corresponding end wall hole and held in tension by the wires 66–72 externally to the mold.

The gel matrix 44, FIG. 3, is formed with the sutures 42 encapsulated in their central regions by the matrix 44. The sutures extend from the contracted gel matrix to form the free ends 52 and 54. The tension in the sutures 42 causes the cells in the matrix 44 to align in the direction of the sutures 42. The contracted gel matrix 44 and sutures 42 form the contracted mat 40. The mat 40 comprises cast MSCs and collagen, for example. The cells may be allogeneic in a further embodiment employing the above procedures and the procedures of the examples herein.

EXAMPLE 4

A mold assembly is used to prepare an implant for repair of a tissue defect in accordance with Example 1. A small, rectangular glass tray-like receptacle, 27 mm×27 mm, forms a glass mold. The glass mold is formed with four spaced parallel grooves cut in the mold bottom wall. Four stiff surgical wires are bent to form small, bow-shaped tension wires with ends shaped to set 2 mm deep into the glass mold, a different wire at each groove. The glass mold is placed into a 100 mm culture dish with a separate suture spanning and corresponding to each tension wire situated in a corresponding groove in the mold in preparation for the gel suspension to be poured. The wires are each attached to a separate corresponding suture and place that suture in tension in the mold.

Preferably autologous undifferentiated mesenchymal cells (MSCs) are suspended in 0.5 ml of 2× DMEM-LG and mixed thoroughly to create a single-cell suspension. Then 0.5 ml sterilized type I collagen solution (Pancogene S™), Gattefossé S A, Lyon, France; 3 mg/ml; dialyzed into 0.001M HCl is added to the cell suspension and pipetted up and down to form a homogenous suspension of cells in the gel. This gel suspension is immediately poured into the prepared glass mold in a culture dish. A lid is placed over the dish and it is put into an incubator at 37° C. to set the gel. After gelation is complete, the dish is flooded with medium without serum until the glass mold is covered and put back into the incubator. Contraction of the gel by the cells occurs to the extent that the gel detaches from the walls of the mold and decreases in thickness, width and length by about 10%. If the cells are cultured in this apparatus for approximately 20 hours, the gel contracts to approximately 60% of its original width and thickness dimensions. At about the 4 hour time point, the gel is firmly attached to the sutures.

Tissue repair devices prepared by this procedure may be implanted in rabbit Achilles tendon defect model either with or without a Vicryl sheath. Histological observations from these implants at 1, 3 and 8 weeks are made to indicate whether neotendon tissues are formed. These early neotendon tissues are morphologically similar to tissues produced from tendon cell or MSC implantation in the Vicryl sheath repair model at later timepoints.

EXAMPLE 5

MSCs and Vitrogen, a commercially available soluble Type I collagen from bovine dermis, available from Collagen Corp., are mixed and cast into a mold around a set of four sutures held in tension as described in Example 4. The gel matrix is allowed to gel and provides cell orientation as in Example 4. The gelled matrix is released from the mold and rolled up into a spiral configuration.

EXAMPLE 6

Same as Example 4 except after initial gelation, the gelled mat and sutures are rolled into a spiral and then the sutures are placed in tension.

EXAMPLE 7

Same as in Example 4 except another layer (or layers) of gelled matrix is introduced. The different layers are rolled together similar to that in FIG. 5. In this way sublayers are introduced that provide control over tissue ingrowth.

EXAMPLE 8

Same as example 7 except the intermediate layer contains an angiogenic factor(s), such as vascular endothelial growth factor, that encourages vascularization along the plane of this intermediate layer without disruption to the other layers.

EXAMPLE 9

Same as previous examples 4–5 except holes are formed in the mat to allow channels for "communication" through the mat. The holes are created post-orientation (will lead to different micro-orientation around the holes). The holes are formed by medical laser drilling after formation of the contracted sheet.

The above spiral rolled methods permit generation of relatively large implants. The overall diameter of the construct can be controlled by a variety of parameters including the thickness of the matrix sheet(s), width of the matrix sheet, and radial tightness of the spiral roll layer about itself. These parameters also have an effect on the tissue growth. While discrete sutures are disclosed in the preferred embodiments, such sutures may also be employed with a fabric support member or, in the alternative, a biodegradable fabric may be employed both as a support member and as sutures in place of discrete sutures. In this case selected filaments of the fabric are preattached to needles and placed under tension in the manner described for discrete sutures. It will occur to one of ordinary skill that various modifications may be made to the disclosed embodiments which are given by way of example without departing from the scope of the invention as defined in the appended claims.

Figure 7:
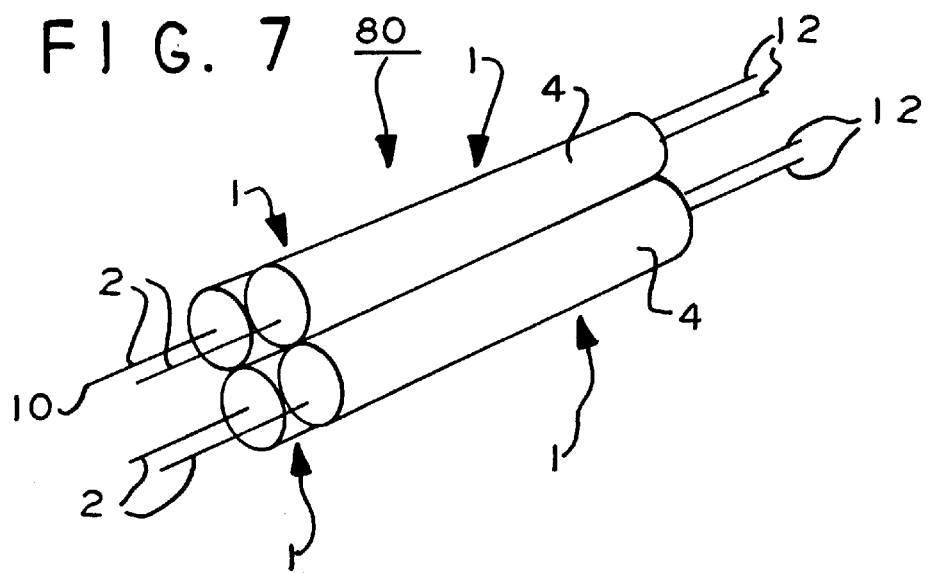
FIG. 7 is an isometric view of a plurality of implants of FIG. 1 in a further embodiment.

In FIG. 7, for example, implant 80 comprises four implants 1 of FIG. 1 in side-by-side parallel contiguous relation. These four implants are implanted as a single construct for a given repair. The implants may also be of the spiral configuration of implant 50, FIG. 5. In a further embodiment, the mat of FIG. 3 may be wrapped about the implant of FIG. 7 to provide an larger implant.

Cited Literature

1. Goodship A E and Cooke P. Bicompatibility of tendon and ligament prostheses. *Critical Reviews in Biocompatibility* 1986;2(4):303–334.
2. Bonnarens F. O. and Drez, D., Jr. Biomechanics of artificial ligaments and associated problems. In: Jackson D W, Drez Jr. D, Eds. *The anterior cruciate deficient knee: New concepts in ligament Repair,* St. Louis: C. V. Mosby Co., 1987;239–253.
3. Goldstein J D, Tria A J, Zawadshy J P, Kato Y P, Christiansen D, Silver F H. Development of a Reconstituted Collagen Tendon Prosthesis: A preliminary study. *J Bone Jt Surig* 1989;71A(8):1183–1191.
4. Hsu S Y C, Cheng J C Y, Chong Y W, Leung P C. Glutaraldehyde-treated bioprosthetic substitute for rabbit Achilles tendon. *Biomaterials* 1989;10:258–264.
5. Kato Y P, Dunn M G, Zawadsky J P, Tria A J, Silver F H. Regeneration of Achilles tendon with a collagen tendon Prosthesis: Results of a one-year implantation study. *J Bone Jt Surg* 1991;73A:561–574.
6. Kato Y P, Dunn M G, Tria A J, Zawadsky J P, Silver F H. Preliminary assessment of a collagen fiber A C L prosthesis. Proceedings of the 17th Annual Meeting of the Society for Biomaterials, Abstract 265, Scottsdale Ariz. 1991.
7. Dunn M G, Tria A J, Kato Y P, Bechler J R, Ochner R S, Zawadsky J P and Silver F H. Anterior cruciate ligament reconstruction using a composite collagenous prosthesis. A biomechanical and histologic study in rabbits. *Am. J. Sports Med.* 1991;20:507–515.
8. Klompmaker J, Jansen H W B, Veth R P H, de Groot J H, Nijenhuis A J, Pennings A J. Porous polymer implant for repair of meniscal lesions: A preliminary study in dogs. *Biomaterials* 1991;12:810–816.
9. Henning C E, Lynch M A, Yearout K M, Vequist S W, Stallbaumer R J, Decker K A. Arthroscopic meniscal repair using an exogenous fibrin clot. *Clin Ortho* 1990;252:64–72.
10. Wood D J, Minns R J, Strover A. Replacement of the rabbit medial meniscus with a polyester-carbon fibre bioprosthesis. *Biomaterials* 1990; 11: 13–16.
11. Stone K R, Rodkey W G, Webber R J, McKinney L, Steadman J R. Collagen-based prostheses for meniscal regeneration. *Clin Ortho* 1990;252:129–135.
12. Grande D A, Pitman M I, Peterson L, Menche 0, Klein M. The repair of experimentally produced defects in rabbit articular cartilage by autologous chondrocyte transplantation. *J Ortho Res* 1989;7:208–218.
13. Grande D A. Technique for healing lesions in cartilage. U.S. Pat. No. 4,846,835, Jul. 11, 1989.
14. von Schroeder H P, Kwan M, Amiel D, Coutts R D. The use of polylactic acid matrix and periosteal grafts for the reconstruction of rabbit knee articular defects. *J Biomed Mat Res* 1991;25:329–339.
15. Wakitani S, Kimura T, Hirooka A, et al. Repair of rabbit articular surfaces with allograft chondrocytes encapsulated in collagen gel. *J Bone Joint Surg* 1989;71–B:74–80.
16. Wang E A, Rosen V, D'Alessandro J S, et al. Recombinant human bone morphogenetic protein induces bone formation. *Biochem* 1990;87:220–224.
17. Syftestad G T, Lucas P A, Ohgushi H, Caplan Al. Chondrogenesis as an in vitro response to bioactive factors extracted from adult bone and nonskeletal tissues. In: Thomhill T, SennA, eds. *Development and diseases of cartilage and bone matrix.,* UCLA Symposium Volume, New York: Alan Liss, Inc., 1987;187–199.
18. Syftestad G T, Lucas P A, Caplan Al. The in vitro chondrogenic response of limb bud mesenchyme to a water-soluble fraction prepared from demineralized bone matrix. *Differentiation* 1985;29:230–237.
19. Lucas P A, Syftestad G T, Caplan A I. A water-soluble fraction from adult bone stimulates the differentiation of cartilage in explants of embryonic muscle. *Differentiation* 1988;37:47–52.
20. Bell E, Ivarsson B, Merrill C. Production of a tissue-like structure by contraction of collagen lattices by human fibroblasts of different proliferative potential in vitro. *Proc Natl Acad Sci USA* 1979;76(3):1274–1278.
21. Guidry C, Hohn S, Hook M. Endothelial cells secrete a factor that promotes fibroblast contraction of hydrated collagen gels. *J Cell Biol* 1990;110:519–528.
22. Klebe R J, Caldwell H, Milam S. Cells transmit spatial information by orienting collagen fibers. *Matrix* 1989;9:451–458.
23. Klebe R J, Overfelt T M, Magnuson V L, Steffensen B, Chen D, Zardeneta G. Quantitative assay for morphogenesis indicates the role of extracellular matrix components and G proteins. *Proc Natl Acad Sci USA* 1991;88:9588–9592.
24. Caplan A I. Effects of the nicotinamide-sensitive teratogen 3-acetylpyridine on chick limb cells in culture. *Exp Cell Res* 1970;62:341–355.
25. Caplan A I, Fink D J, Goto T., Linton A E, Young R G, Wakitani S, Goldberg V M, Haynesworth S E. Mesenchymal Stem Cells and Tissue Repair In: Jackson D W et al., eds. *The Anterior Cruciate Ligament: Current and Future Concepts,* New York: Raven Press, Ltd., 1993; 405–417.

What is claimed is:

1. An implant for repair of a tissue defect in an animal in need thereof, said implant comprising:
    a contracted gel matrix formed in a planar mat having a length and a width forming a broad surface and a thickness relatively smaller than said width and length; and
    mesenchymal stem cells within said contracted gel matrix, said cells having contracted said gel matrix in tension in a given direction.
2. The implant of claim 1 including at least one elongated load bearing support member extending in the given direction through and embedded within the matrix and having free opposing ends extending beyond the contracted matrix.
3. The implant of claim 1 wherein said cells are human mesenchymal stem cells (MSC).
4. The implant of claim 1 wherein the mat is rolled against itself and formed into a spiral roll configuration.
5. The implant of claim 2 wherein said at least one elongated load bearing support member includes a plurality of support members in spaced side by side relation in the mat, each member having adjacent free opposing ends.
6. The implant of claim 5 wherein the support members are biodegradable filaments.
7. The implant of claim 6 wherein the cells are human mesenchymal stem cells.

8. The implant of claim 7 wherein the mat is rolled against itself into a spiral configuration.

9. The implant of claim 2 wherein the at least one load bearing member is preloaded in tension along the given direction during contraction of the gel matrix.

10. The implant of claim 2 wherein the at least one load bearing member is selected from the group consisting of a single filament, multiple filaments, biodegradable fibrous materials, woven filaments, collagen fibers and at least one flexible, pliable filament.

11. An implant for repair of a tissue defect in an animal in need thereof, said implant comprising:

a contracted gel matrix formed in a mat sheet;

mesenchymal stem cells (MSCs) within said contracted gel matrix, said cells having contracted said gel matrix in tension in a given direction; and a plurality of support members extending in the given direction through and embedded within the matrix, each member having opposing free ends extending beyond the contracted matrix.

12. The implant of claim 11 wherein the sheet is rolled about itself into a spiral so that the opposing free ends at each end are adjacent to each other.

13. The implant of claim 11 wherein the support members comprise biodegradable filaments.

14. The implant of claim 11 wherein the MSC cells are human mesenchymal stem cells.

15. An implant for repair of a tissue defect in an animal in need thereof, said implant comprising:

a contracted gel matrix formed as a flat mat; and a plurality of load bearing support members lying encapsulated in the gel matrix, the support members having opposite end portions extending from the matrix, the support members extending in a given direction; and mesenchymal stem cells within said contracted gel matrix, said matrix having been contracted by said cells in tension in said given direction.

16. The implant of claim 15 wherein the cells are human mesenchymal stem cells (MSC).

17. The implant of claim 15 wherein the contracted gel matrix and load bearing support members are rolled into a spiral terminating at first and second opposite ends, said load bearing support members extending from each said opposite ends.

18. An implant for repair of a tissue defect in an animal in need thereof, said implant comprising:

a contracted gel matrix formed as a flat mat and rolled against itself into a spiral;

at least one load bearing support member lying encapsulated in the gel matrix, the support member comprising a discrete support filament having opposite end portions extending from the matrix, the support filament extending in a given direction; and mesenchymal stem cells within said contracted gel matrix, said matrix having been contracted by said cells in tension in said given direction.

19. The implant of claim 18 wherein the cells are human mesenchymal stem cells.

20. The implant of claim 18 including a plurality of said mats formed into said spiral roll in overlying contiguous relation.

21. The implant of claim 18 including a plurality of said contracted gel matrices disposed in parallel adjacent relationship to one another.

* * * * *

UNITED STATES PATENT AND TRADEMARK OFFICE
CERTIFICATE OF CORRECTION

PATENT NO. : 6,174,333 B1
DATED : January 16, 2001
INVENTOR(S) : Kadiyala et al.

It is certified that error appears in the above-identified patent and that said Letters Patent is hereby corrected as shown below:

Title page,
Item [75], Inventors, change "Randall G. Young" to -- Randell G. Young --

Column 1,
Line 5, insert -- This invention was made with government support under SBIR Phase II grant number R44 AR 42618 awarded by the National Institutes of Health. The government has certain rights in the invention. --

Signed and Sealed this

Seventh Day of September, 2004

JON W. DUDAS
*Director of the United States Patent and Trademark Office*